US012156845B2

(12) United States Patent
Thorisdottir et al.

(10) Patent No.: US 12,156,845 B2
(45) Date of Patent: Dec. 3, 2024

(54) LOCKING AND ADJUSTMENT MECHANISM FOR EXOSKELETON

(71) Applicant: OSSUR ICELAND EHF, Reykjavik (IS)

(72) Inventors: Kristin Asa Thorisdottir, Reykjavik (IS); David Sandahl, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 638 days.

(21) Appl. No.: 17/604,632

(22) PCT Filed: Apr. 23, 2020

(86) PCT No.: PCT/US2020/029573
§ 371 (c)(1),
(2) Date: Oct. 18, 2021

(87) PCT Pub. No.: WO2020/219712
PCT Pub. Date: Oct. 29, 2020

(65) Prior Publication Data
US 2022/0192912 A1  Jun. 23, 2022

(51) Int. Cl.
*B25J 9/00* (2006.01)
*A61H 3/00* (2006.01)
*A61H 1/02* (2006.01)

(52) U.S. Cl.
CPC .............. *A61H 3/00* (2013.01); *B25J 9/0006* (2013.01); *A61H 1/0244* (2013.01); *A61H 2003/007* (2013.01)

(58) Field of Classification Search
CPC ............. B25J 9/0006; A61H 2003/007; A61H 1/0274; A61H 1/0255; A61H 1/0244; A61H 1/024; A61H 1/0237
See application file for complete search history.

(56) References Cited

U.S. PATENT DOCUMENTS 6,609,642 B2 * 8/2003 Heinz ....................... A45F 3/00
224/628
6,926,685 B1 * 8/2005 Modglin ................. A61F 5/022
602/5

(Continued)

FOREIGN PATENT DOCUMENTS

WO  2016128877 A1  8/2016

OTHER PUBLICATIONS

International Search Report and Written Opinion from PCT Application No. PCT/US2020/029573, Sep. 28, 2020.

*Primary Examiner* — Alvin J Stewart
(74) *Attorney, Agent, or Firm* — Workman Nydegger

(57) ABSTRACT

An exoskeleton system includes a body interface and connects to a power supply. The body interface and the power supply include a quick lock connection mechanism arranged to adjust to the height and width of a user. The body interface includes a connection frame that defines at least two anchoring slots at different heights for connecting to corresponding anchors extending from the power supply. The power supply includes a removable locking element for securing the anchors to the anchoring slots at a selected height position. The power supply may have transmission arms driven by a drive system, and an assistive system for connection to a user. The transmission arms may be slidably connected to the drive system and have a locking part to secure the power supply in a plurality of predetermined width positions.

20 Claims, 10 Drawing Sheets

(56) References Cited

U.S. PATENT DOCUMENTS

| | | | | |
|---|---|---|---|---|
| 7,316,660 | B1* | 1/2008 | Modglin | A61F 5/028 602/5 |
| 7,329,231 | B2* | 2/2008 | Frank | A61F 5/028 602/19 |
| 8,006,877 | B2* | 8/2011 | Lowry | A45F 3/04 224/660 |
| 8,172,779 | B2 | 5/2012 | Ingimundarson et al. | |
| 8,795,215 | B2* | 8/2014 | Rossi | A61F 5/026 602/5 |
| 8,968,222 | B2* | 3/2015 | Kazerooni | B25J 9/0006 224/265 |
| 9,504,596 | B1* | 11/2016 | Kozersky | A61F 5/028 |
| 2003/0000986 | A1* | 1/2003 | Smith | A45F 3/14 224/637 |
| 2014/0207041 | A1* | 7/2014 | Ingimundarson | A61F 5/0193 602/23 |
| 2015/0335515 | A1* | 11/2015 | Lee | A61H 1/0244 601/5 |
| 2017/0007435 | A1 | 1/2017 | Klutts | |
| 2017/0049659 | A1 | 2/2017 | Farris et al. | |
| 2018/0200878 | A1* | 7/2018 | Tsai | A61F 2/70 |
| 2018/0257216 | A1* | 9/2018 | Shavit | B25J 9/0006 |
| 2018/0280183 | A1 | 10/2018 | Ingimundarson et al. | |
| 2018/0325764 | A1 | 11/2018 | Yagi | |
| 2019/0091094 | A1 | 3/2019 | Romo et al. | |
| 2019/0118372 | A1* | 4/2019 | Sasaki | B25J 9/101 |
| 2019/0183713 | A1 | 6/2019 | Sankai | |
| 2019/0201274 | A1* | 7/2019 | Teng | A61H 3/00 |
| 2019/0254914 | A1* | 8/2019 | Nam | A61H 1/0262 |
| 2020/0281796 | A1* | 9/2020 | Lakany | A61H 1/0277 |
| 2021/0220207 | A1* | 7/2021 | Kim | B25J 9/0006 |
| 2021/0237258 | A1* | 8/2021 | Tourneux | B25J 9/0006 |
| 2021/0237259 | A1* | 8/2021 | Moise et al. | B25J 9/106 |
| 2022/0354730 | A1* | 11/2022 | Garcia Armada | A61H 1/0262 |
| 2022/0401284 | A1* | 12/2022 | Arzanpour | A61H 1/024 |
| 2023/0330835 | A1* | 10/2023 | Livolsi | A61H 3/00 |

* cited by examiner

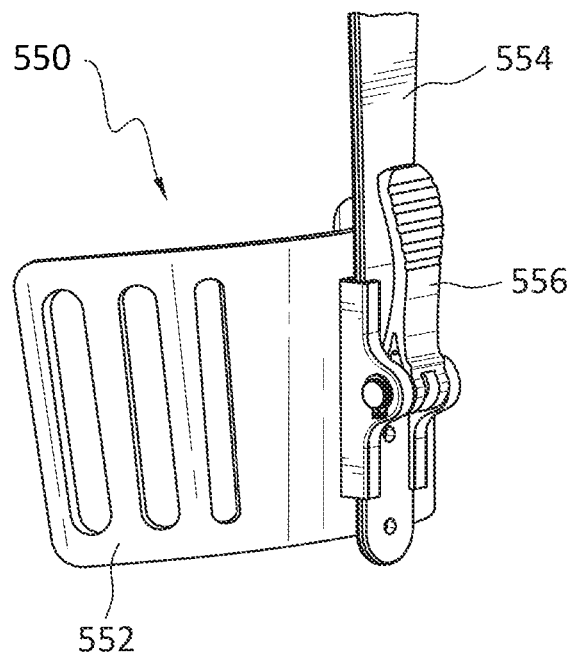
FIG. 14A
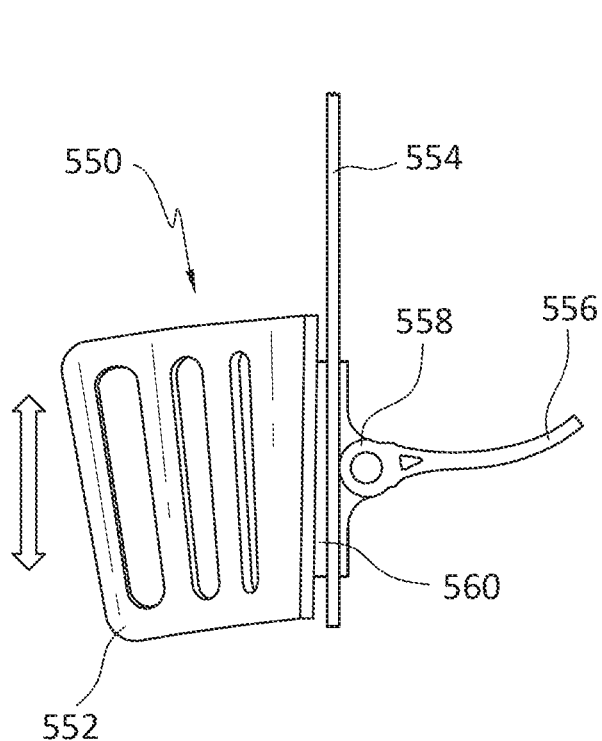 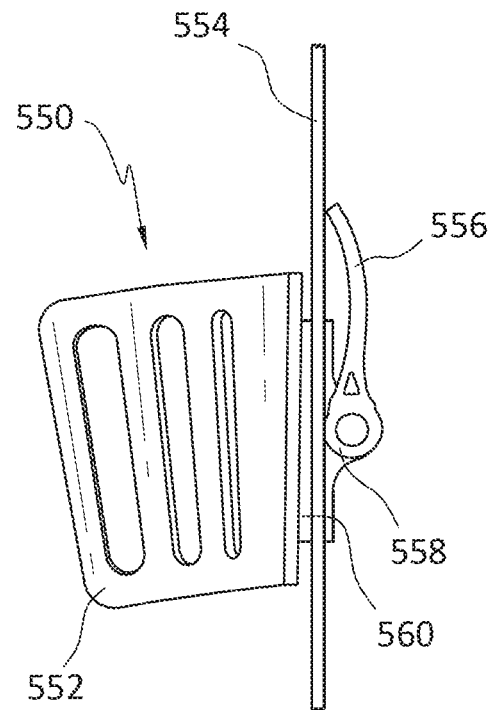
FIG. 14B
FIG. 14C

LOCKING AND ADJUSTMENT MECHANISM FOR EXOSKELETON

FIELD OF THE DISCLOSURE

A locking and adjustment mechanism for use with a body interface, usable as an anterior-posterior orthosis, and a power supply of an exoskeleton having improved adjustability and means for proper donning and doffing, the body interface and a power supply being by example an active pelvic orthosis (APO).

BACKGROUND

Exoskeletons are becoming useful tools for addressing needs in healthcare and industrial applications. These exoskeletons can give a user improved endurance and stability or can provide corrections to an impaired individual's gait by applying mechanical forces to the body in parallel with the user's muscles. These assistive and rehabilitative bionics technologies have the potential to improve quality of life, reduce the incidence of injury, and create a safer, more comfortable, and productive environment. Exoskeletons may be used in other applications such as in the fitness and exercise domain, whereby the exoskeleton may be arranged to provide restrictive or resistive forces during movement to improve the strength and endurance of a user.

An example of an exoskeleton is an active pelvis orthosis (APO), which is a wearable exoskeleton arranged to improve gait energy efficiency, especially as affected by impairments of the hip. The APO may be of the type described in WO 2016/128877, which employs a sophisticated system of links, actuators, and other components to allow the human flexion-extension axis to align with the control systems to give the user hip abduction/adduction rotation, and internal/external rotation assistance. The APO further includes a human interface to ensure comfort despite activation by the control system of the user's joints by the exoskeleton.

A recognized impediment to developing these exoskeletons is the complexity of adjusting the system to an individual user, both during use and in manufacture. These devices must achieve optimal kinematic coupling and compatibility between the human joints and rotation axes of the exoskeleton. As body dimensions and assistive requirements can vary widely among users and over time, an exoskeleton must be arranged and configured differently according to the needs of the user.

Donning and doffing, with ease and accuracy of adjustability, are often challenges for the practical use of exoskeletons, particularly in healthcare applications where an impaired user may have physical limitations and require frequent adjustment as part of a treatment regime. The difficulty of conforming to an exoskeleton, which includes rigid powered elements, to the physical dimensions of a user's body comfortably and effectively generally requires the assistance of multiple technicians, and costly precision manufactured components and significant time expenditures.

Most exoskeletons comprise at least three components: a frame, a power supply including an actuation system, and a physical body interface (often including straps, bindings, etc.). The power supply may include a power source and control system for driving the actuation system. Assembly of the components may be complicated, and, when assembled, the resulting exoskeleton may be large, heavy, and unwieldy.

In the instance of exoskeletons, including the actuation system, such as powered actuators by the power supply or motion modules, these systems are deficient in offering adjustability for and convenience in adequately placing the power supply over the body of a user. Typically, the power supply is supported by a user along their back to minimize interference with motion of limbs and to facilitate carrying of the power supply.

These actuation systems are costly, and it is challenging to provide off-the-shelf or easy to manufacture systems that can adapt to the widely differing dimensions of different users, especially if different users wear the exoskeleton successively during healthcare or industrial applications. Likewise, assembling these systems on the body of the user is complicated, and requires the manual manipulation of individual connection points to ensure a secure connection. Existing devices poorly address these issues, as the power supply of the exoskeleton is often fixedly attached to the body interface, requiring the manipulation of several screws for adjustment and secure attachment, or being incapable of individual adjustment.

The body interface also should be customized to an individual's contours and anatomical needs, and the body interface should be adjustable to fit dimensions with different users. Existing devices fail to provide an adjustable interface between a body and an exoskeleton that can conform to varying dimensions, contours, and other anatomical needs of different user's without sacrificing effective engagement.

From the foregoing discussion, there is a need for a body interface and power supply suitable for assembly as an exoskeleton, including a quick and straightforward locking system configured for attachment at multiple points to assist in a stable and secure assembly of the exoskeleton rapidly. There is further a need for a power supply suitable for an exoskeleton having improved adjustability and ease in donning and doffing.

SUMMARY

According to embodiments of the disclosure, the body interface and the power supply are provided with a quick locking connection system as an improvement over known connection mechanisms of an exoskeleton, with increased speed and adjustability of assembly. While described in a body interface and a power supply of an exoskeleton, the embodiments disclosed and the individual components thereof may likewise be extended to other systems, braces, and supports in orthopedics, such as a spinal orthosis or an upper-body orthosis.

The embodiments of the body interface may include a panel that serves as a frame for the body interface. The panel may be an anatomically-shaped substrate formed from a rigid or semi-rigid material and may be provided with a connection frame for securing to the actuation system. The body interface and/or the panel may be configured as a lumbar support for increased comfort by conforming to a user's anatomical shape. The body interface and/or the panel improves comfort and long-term use by reducing abrasion against a user by evenly distributing forces to avoid pressure points, and by enhancing breathability and ease of donning and doffing.

The connection frame of the panel may be arranged with a plurality of anchoring points, such as recesses, slots, or the like, for attaching to the actuation system. Embodiments of the power supply are provided with corresponding anchors, such as in hooks or protrusions, for securing to the anchoring points of the connection frame. The anchoring points and anchors increase the ease of assembly of the power supply with the body interface, enabling a rapid and straightforward connection that only requires lowering the power supply against the body interface.

The arrangement of a plurality of upper and lower anchoring points on the connection frame allows for varying the height of the connection between the body interface and the actuation system, without requiring a change in the components themselves. It stabilizes the power supply on the body interface during use.

The power supply may further be provided with a locking element that can secure the power supply in place on the body interface. The locking element may be engaged by a technician while lifting the actuation system, so the locking element does not increase the complexity of donning and doffing.

The power supply may include a width adjustment mechanism, so a width of the power supply may be increased or decreased by slidably moving a transmission device. A drive locking element may be provided to lock the width of the power supply in preset positions. It may be disengaged by a technician to adjust the width of the power supply while the device is secured to the body interface.

Embodiments of the body interface and power supply are adapted to anatomically improve donning and doffing of the exoskeleton system, and adjustability to a user's height and width dimensions. The locking elements preferably are spring actuated to yield an easily adjustable system that is adjustable by a single technician during donning and doffing, or while components of the exoskeleton system are in place.

The locking elements and anchors of the body interface and the activation system allow adjustment of the system and donning and doffing without additional tools or materials. The body interface and power supply further have versatility for use on a variety of individuals having different dimensions in rapid succession, while preserving a secure and stable attachment of the system to the user's body.

The above embodiments solve the problem of existing exoskeletons, including actuation systems and body interfaces, having complex and costly connection mechanisms by providing an improved power supply and body interface with increased adjustability and simplicity. The improved power supply and body interface combining high adjustability in a height and width dimension with increased simplicity and stability for users with truncal weakness or different activities.

BRIEF DESCRIPTION OF THE DRAWINGS

FIG. 14A is a perspective view of an embodiment of a leg connection.

FIG. 14B is a schematic view of a leg connection of FIG. 14A in an unlocked mode.

FIG. 14C is a schematic view of a leg connection of FIG. 14A in a locked mode.

Figure 1A:
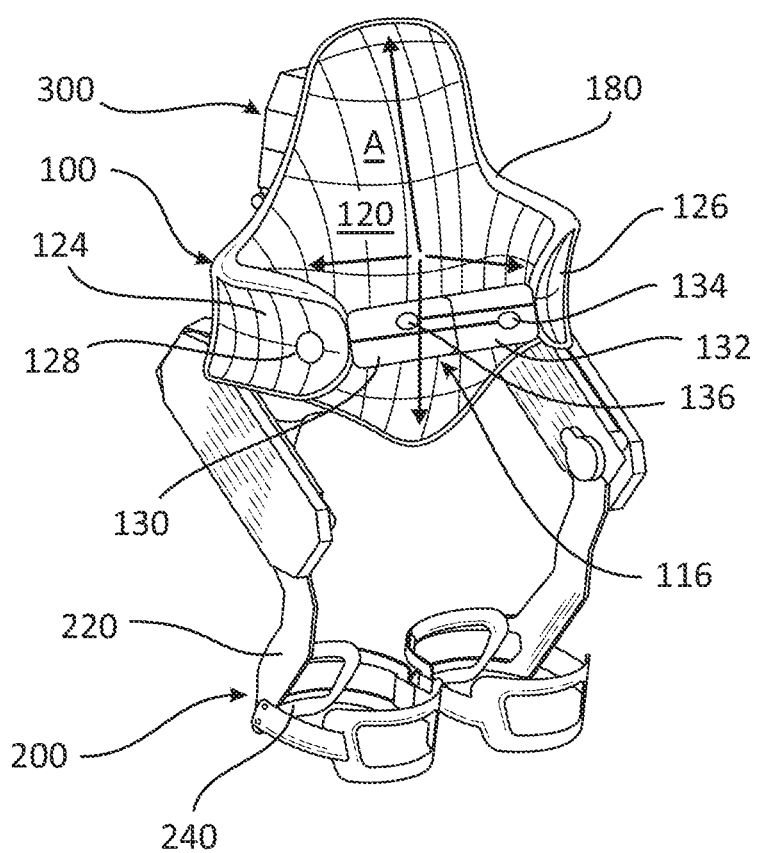
FIG. 1A is a schematic view of an exoskeleton, including a body interface and a power supply according to embodiments of the disclosure.

The drawings and figures are not drawn to scale, but instead are drawn to provide a better understanding of the components, and are not intended to be limiting in scope, but to provide exemplary illustrations. The figures illustrate exemplary configurations of a body interface, and in no way limit the structures or configurations of a body interface and components according to the present disclosure.

DETAILED DESCRIPTION OF VARIOUS EMBODIMENTS

A better understanding of different embodiments of the disclosure may be had from the following description read with the drawings in which like reference characters refer to like elements.

While the disclosure is susceptible to various modifications and alternative constructions, certain illustrative embodiments are in the drawings and are described below. The dimensions, angles, and curvatures represented in the introduced above are to be understood as exemplary and are not necessarily shown in proportion.

It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an actuation system and variants as disclosed, a description of a few terms may be useful. The embodiments of the actuation system may correspond to anterior and posterior body sections defined by an anterior-posterior plane and lateral body sections defined by a medial or sagittal plane. The anatomical terms described are not intended to detract from the normal understanding of such terms as readily understood by one of ordinary skill in the art of orthopedics, braces, human interfaces, and supports.

These anatomical terms follow the user wearing the actuation system, referring to an anatomical position. An anatomical position is generally defined as the erect position of the body with the face directed forward, the arms at the side, and the palms of the hands facing forward, and which is a reference in describing the relation of body parts to one another.

The terms "rigid," "flexible," "compliant," and "resilient" may distinguish characteristics of portions of certain features of the actuation system. The term "rigid" should denote that an element of the actuation system, such as a frame, is generally devoid of flexibility. Within the context of features that are "rigid," it should indicate that they do not lose their overall shape when force is applied and may break if bent with sufficient force. The term "flexible" should denote that features are capable of repeated bending so the features may be bent into retained shapes or the features do not retain a general shape, but continuously deform when force is applied.

The term "compliant" may qualify such flexible features as generally conforming to the shape of another object when placed in contact in addition to that, via any suitable natural or applied forces, such as gravitational forces, or forces applied by external mechanisms, for example, strap mechanisms. The term "resilient" may qualify such flexible features as generally returning to an initial general shape without permanent deformation. As for the term "semi-rigid," this term may connote properties of support members or shells that provide support and are free-standing; however, such support members or shells may have flexibility or resiliency.

The embodiments of the disclosure are adapted for a human body and may be dimensioned to accommodate different types, shapes, and sizes of human body sizes and contours. For explanatory purposes, the actuation system embodiments described are referred to as corresponding to different sections of a body and are denoted by general anatomical terms for the human body.

The embodiments of the disclosure relate to a connection system of a body interface and power supply for use with an exoskeleton system having improved adjustability and improved means for proper donning and doffing, resulting in a quick and simple assembly with high precision coupling and compatibility between human joints and rotation axes of the exoskeleton system.

The exoskeleton system may incorporate features in a hip orthosis or actuation system, such as a hip orthosis or actuation system disclosed in PCT/IB2016/050639, filed on Feb. 8, 2016, and published as WO 2016/128877 A1 on Aug. 18, 2016, which is incorporated by reference.

The body interface may incorporate features in a spinal orthosis, such as a spinal orthosis disclosed in U.S. patent application publication 2017/0007435, published on Jan. 12, 2017 and incorporated by reference. However, unlike in a spinal orthosis that is specifically designed for pain relief, protecting injured ligaments or muscles, and post-surgical immobilization, the body interface of the embodiments of the disclosure are provided for the support over soft tissue while permitting mechanical actuators to assist the motion of skeletal structures. The body interface, like the known spinal orthosis, may be configured to relieve pressure over the spinous processes while applying even pressure to the paraspinal musculature to ensure comfortable support of the exoskeleton equipment.

A known spinal orthosis, such as the exemplary spinal orthosis described in U.S. Pat. No. 8,172,779, granted on May 8, 2012, and incorporated by reference, and the embodiments of the body interface, have outer and inner side configurations, with the inner side arranged to be adjacent to the user's back. The orthosis and body support have first and second belt members, and a compression or closure system adapted to exert pressure onto the lumbar region of a user's back. The compression or closure system includes tightening elements or drawstrings that permit the user to adjust pressure over the back and a cover extending over the compression system.

While in the spinal orthosis a flexible or semi-rigid back plate extend over at least part of the compression system, the body interface preferably has a rigid or semi-rigid frame that may include a posterior panel arranged to be adjacent to the back of the user and to carry an actuation system, such as including actuators and/or a power supply. An anterior panel may be attached to the body interface on an anterior side thereof.

Referring to FIG. 1A, an exoskeleton includes a body interface 100, an assistive system 200, and a power supply 300. The power supply 300 includes a housing 301. In an assembled condition, the body interface 100 is fitted to a user and adjusted for comfort and stability. At the same time, the power supply 300 is connected to the body interface 100 and configured for driving the assistive system 200. The assistive system 200, according to embodiments of the disclosure may include straps, joints, and other supports configured to the joints of the user's body, in FIGS. 1A and 1B, the assistive system 200 includes a leg/hip assist mechanism 220 and a leg connection 240, preferably on lateral sides of the body interface 100, for attachment to the body of a user. The assistive system 200 may incorporate features of an APO, or similar systems, such as described in WO 2016/128877A1.

The body interface 100 includes a frame, as in a panel 180 that is semi-rigid or rigid, and may be configured as a lumbar support. As a lumbar support, the body interface 100 may be tensionable to a shape and width of a user over a sacral area and may be provided with additional padding, configurable supports or panels and/or a cover 120. The body interface 100 is stabilized on a user's muscle and soft-tissue, while remaining stable in position on the user according to relative movement of the assistive system 200 attachable to the power supply 300 and/or the body interface 100, for providing stability of without sacrificing comfort or adaptability.

The panel 180 of the body interface 100 may be arranged to control sagittal movement, reducing gross and intersegmental flexion and extension of the hip(s) and trunk. The panel 180 may be arranged to control coronal movement (with the arms) to control spinal/hip motion of lateral bending and abduction, respectively. The panel 180 may likewise be arranged to control the flexion-extension movement.

The body interface 100 and/or the panel 180 may incorporate features of a spinal orthosis and/or features of a body interface, such as disclosed in U.S. patent application publication 2018/0280183, published on Oct. 4, 2018, and U.S. patent application publication 2019/0091094, published on Mar. 28, 2019, which are incorporated herein by reference. For example, the panel 180 may be provided with lateral supports, a top portion, notches for facilitating bending, and/or tapered extensions corresponding to a lumbar region of the user. At the same time, the body interface 100 may be configured as a lumbar support.

FIG. 1A shows the body interface 100 including first and second arms 124, 126 on opposed lateral sides of the panel 180 through which first and second belt segments 130, 132 of an attachment system 116, respectively, extend to engage one another. At least one tensioning element 134, 136 is movable relative to the panel 180 to tension the attachment system 116 by reducing the circumference thereof. The at least one tensioning element 134, 136 secures to one of the first and second belt segments 130, 132 of the attachment system 116 and is adapted to move the first and second belt segments 130, 132 relative to the panel 180. The first and second arms 124, 126 are preferably curved, so the first and second arms generally hug or closely embrace the body of the user. Such a configuration aids the donning and assures that the body interface 100 remains securely on the user. The at least one tensioning element is optional, and the body interface 100 may be provided without such at least one tensioning element.

The at least one tensioning element 134, 136 may be arranged similarly as in U.S. patent application publication 2017/0007435.

Figure 1B:
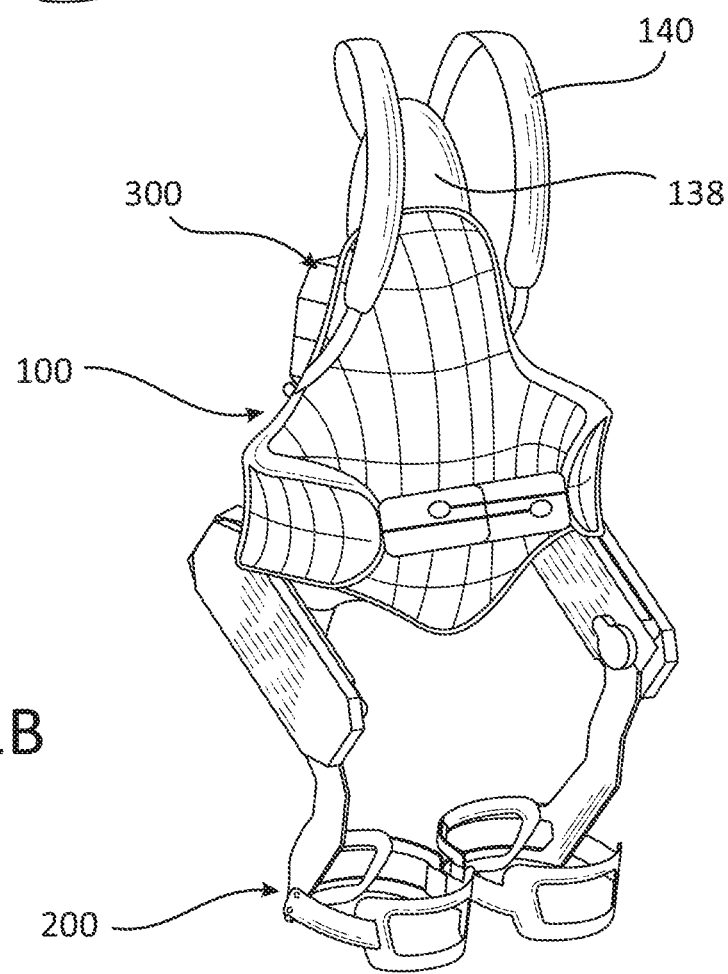
FIG. 1B is a schematic view of the exoskeleton of FIG. 1A, including a posterior panel extension.
Figure 2:
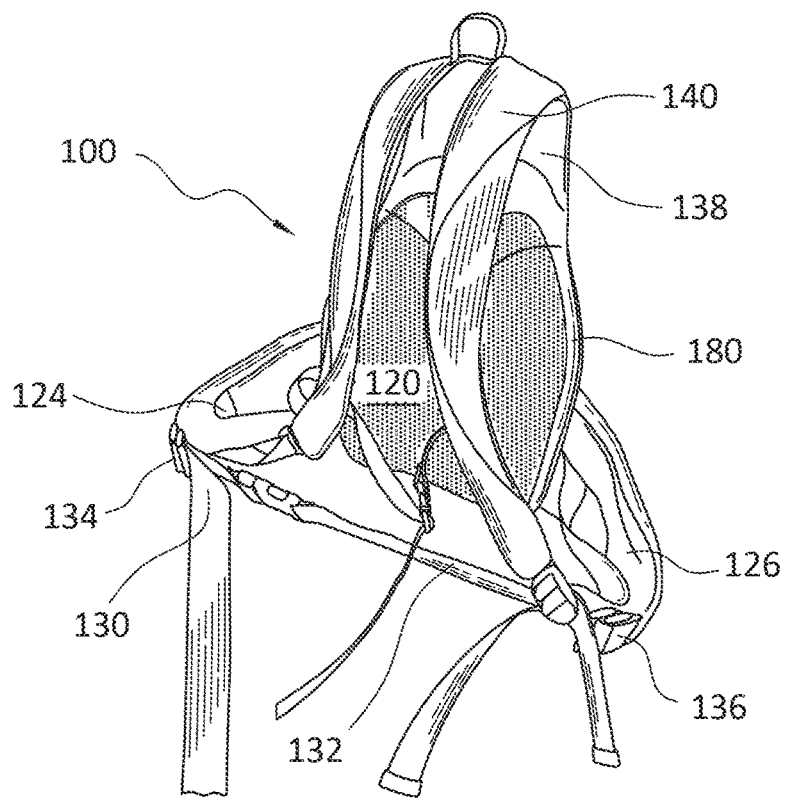
FIG. 2 is a perspective view of an embodiment of the body interface of FIG. 1B.

As shown in FIGS. 1B and 2, the body interface 100 may include a panel attachment 138 for attaching to the panel 180 superiorly, the panel attachment 138 including a strap system 140. In a variation, the panel 180 may have stretchable components or segments. The panel 180 and/or the body interface 100 may be static because it is not adjustable in tension aside from bearing weight from a user, or it may be dynamically adjustable because of additional components that are tensionable relative to the panel 180 by one or more tensioning devices 128.

In use, the body interface 100 may be donned like conventional lumbar supports or to a backpack type interface. For example, the body interface 100 may be donned by passing the arms of a user through the strap system 140, tightening the straps against shoulders of the user, and tensioning the attachment system 116 about the user's torso. The body interface 100 should be securely attached to the body of the user by adjustable tension, such as described in U.S. patent application publication 2019/0091094, to provide a secure and comfortable base for the power supply 300.

The body interface 100 or components thereof may be provided in a plurality of different sizes, as manufacturing the body interface 100 is generally less expensive than other components of the exoskeleton. For example, the body interface 100 may be provided in small, medium, and large sizes so that a technician may select the appropriate body interface 100 for a user.

Figure 3:
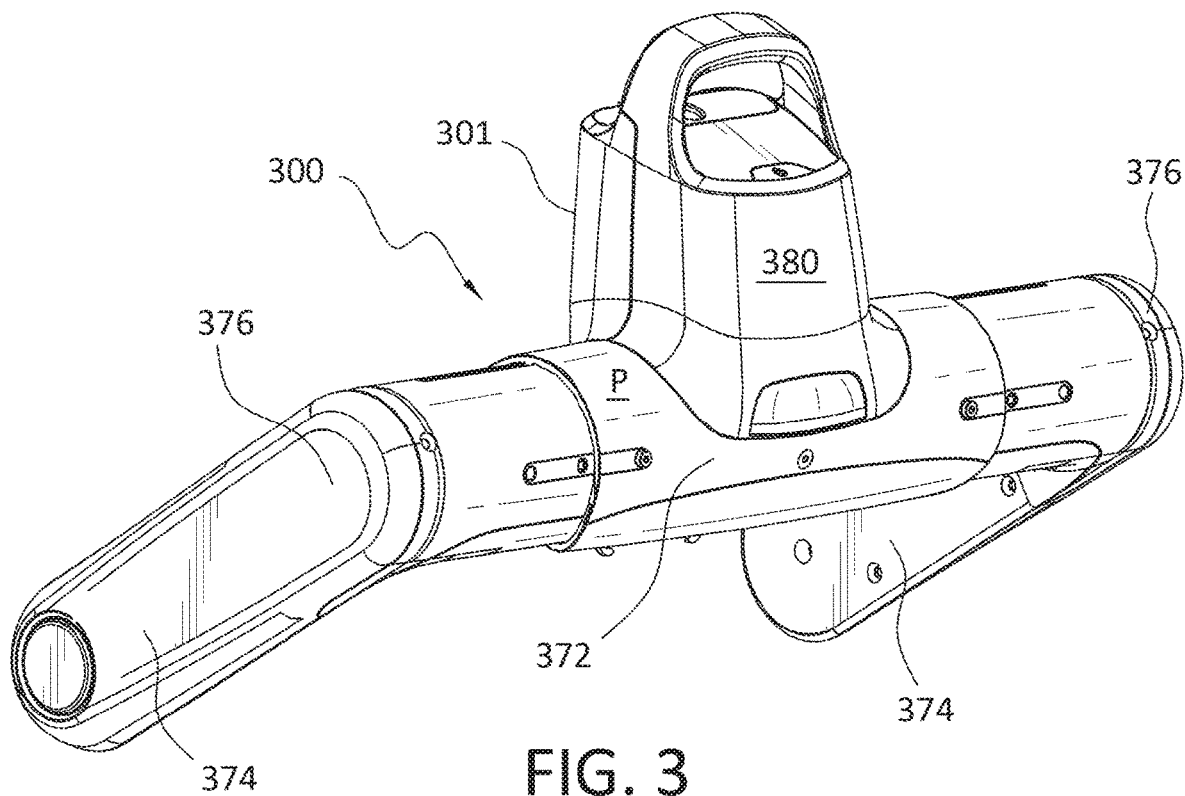
FIG. 3 is a rear perspective view of a power supply according to embodiments of the disclosure.

FIG. 3 generally illustrates an embodiment of the power supply 300, or actuation system, for an exoskeleton according to the disclosure. The power supply 300 includes a drive system 372 linked to a transmission device 374, for example, by a passive joint mechanism, and driven by a power system 380, for example, including a motor, a control unit, and/or a power supply. The transmission arms 374 are arranged to be driven by the drive system 372. The assistive system 200 is secured to the transmission device 374, so the assistive system 200 is controlled and/or powered thereby. As illustrated in the embodiment, according to FIG. 3, the power supply may be an APO and include robotic hip joints 376.

Figure 4:
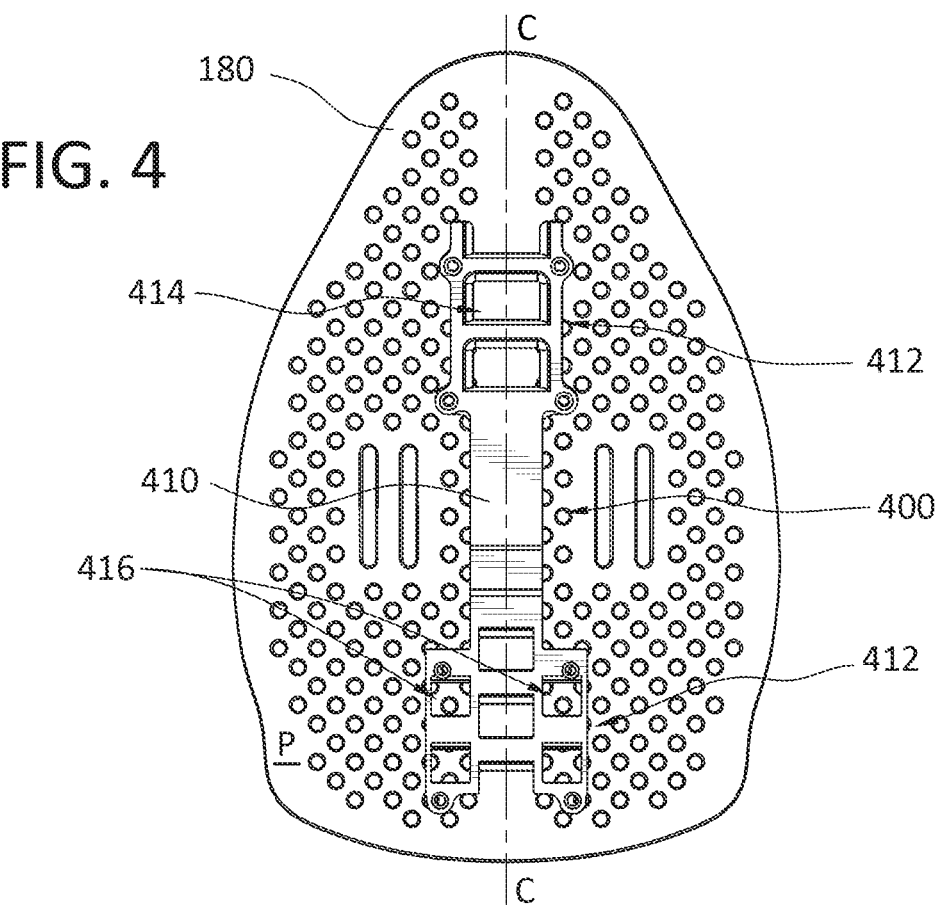
FIG. 4 is a schematic view of a panel, including a panel connection system for the body interface according to FIGS. 1A and 1B.

The housing 301 of the power supply 300 is preferably connected to a posterior side P of the body interface 100 by a quick lock connection system 400, opposite an anterior side A arranged for contacting the body of the user. As shown in the embodiment of FIG. 4, the quick-lock connection system 400 may include a connection frame 410 integrated in the panel 180 of the body interface 100, such as with bolt connectors, screw connectors, molding or other integration methods. The connection frame 410 is provided with at least one anchor point 412 for receiving at least one corresponding anchor 312 of the power supply 300.

In an embodiment, the at least one anchor point 412 may include a slot or recess and the corresponding anchor 312 may include a protrusion or hook for securing to and/or about the anchor point 412. By providing the at least one anchor point 412 and the corresponding anchor 312 in a slot and hook, a secure and fast attachment of the connection system 400 is enabled simply. In use, a technician is only required to lift the power supply 300 and lower it against the body interface 100 to secure the anchor 312 to the anchor point 412, fixing the power supply to the panel 180 of the body interface 100 by a downward force of gravity.

The anchor 312 of the power supply 300 and the anchor point 412 may be configured to have complementary shapes. For example, the anchor 312 may be adapted as a hook-shaped protrusion having a downwardly or upwardly protruding lip, and the anchor point 412 configured as a slot, so the anchor 312 is adapted to secure to the anchor point 412 on at one side. In a preferred embodiment, the anchor point 412 and the corresponding anchor 312 are arranged to have substantially equivalent and/or cooperating relative dimensions, for example in a lateral direction, so the movement of the power supply 300 relative to the body interface 100 is substantially prevented in at least one direction.

Figure 5:
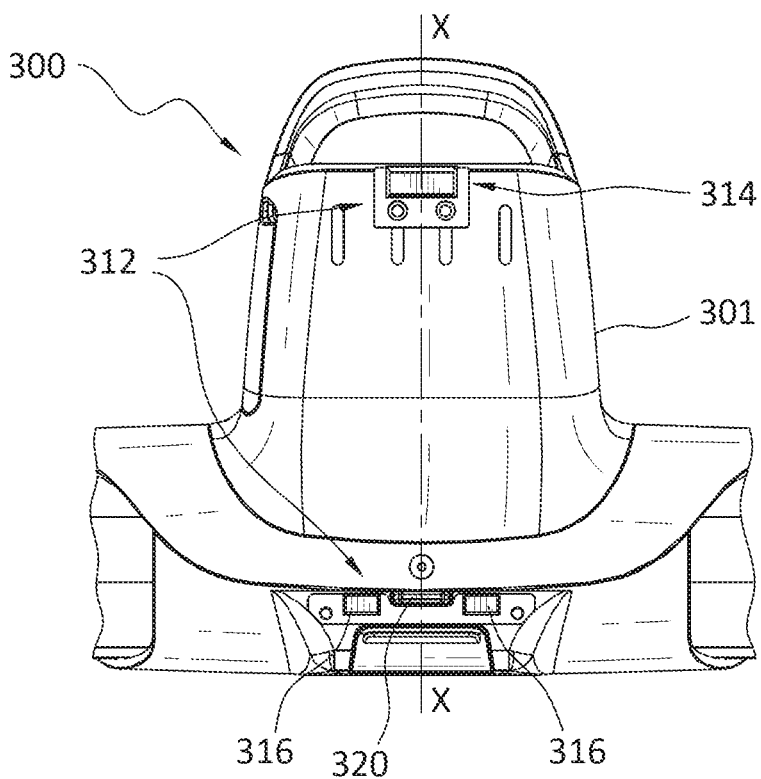
FIG. 5 is a front schematic view of the power supply of FIG. 3, including a power supply connection system.

The connection frame 410 may have at least two anchor points 412, possibly including at least one upper anchor point 414 and at least one lower anchor point 416, such as with a matching alignment of at least one upper corresponding anchor 314 and at least one lower corresponding anchor 316 on the power supply 300, as shown in FIG. 5. According to the embodiment of FIG. 4, the upper anchor point 414 may be provided along a center axis C, for example corresponding to a mid-sagittal plane of the user. In contrast, one of the two lower anchor points are positioned at each lateral side of the center axis C to form a three-point attachment. Such a three-point attachment with laterally offset anchor points 412 limits motion of the power supply 300 relative to the body interface 100 when secured together, while preserving a simple arrangement for matching the anchors 312, 314, 316 of the power supply to the anchor points 412, 414, 416 on the connection frame 410.

In use, the power supply 300 may generate an actuation force for the assistive system 200, so torque is generated against the body interface 100. Where a less secure attachment is used, such as using a strap system or an attachment in only a single plane, the generated torque may cause relative motion, shaking, vibration, or even the disconnection of the power supply 300 relative to the body interface 100. Where the exoskeleton is used in industrial or healthcare applications, high precision of movement is required, and excess motion, such as lateral motion, shaking or vibration, may cause imbalance or other difficulties to a user.

The three-point attachment of FIG. 4 enables increased accuracy in the positioning of the power supply 300 relative to the body interface 100. It increases the stability of the attachment against the generated torque, so a secure and reliable attachment of the power supply 300 is achieved with a relatively easy assembly motion. Additional configurations are possible, as understood by one of ordinary skill in the art because of the illustrated embodiments, and the three-point configuration shown is exemplary.

Figure 6:
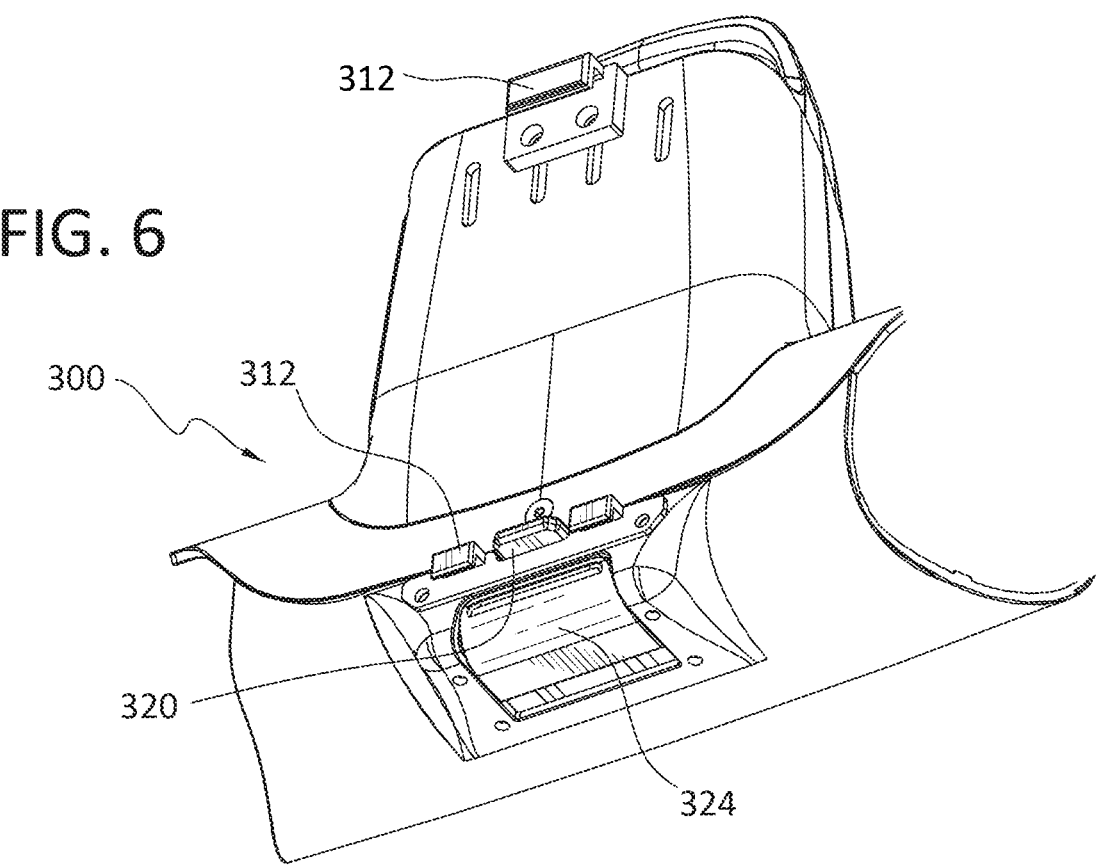
FIG. 6 is a lower perspective view of the power supply and the power supply connection system of FIG. 5.

As illustrated in the embodiment of FIGS. 5 and 6, the power supply 300 may be provided with a locking element 320 for securing the power supply 300 on the connection frame 410, for example, against an upward force. The locking element 320 may be movable relative to the power supply 300 into a locking position or an unlocking position, for removably engaging with a locking point 420 provided on the connection frame 410.

Figure 7:
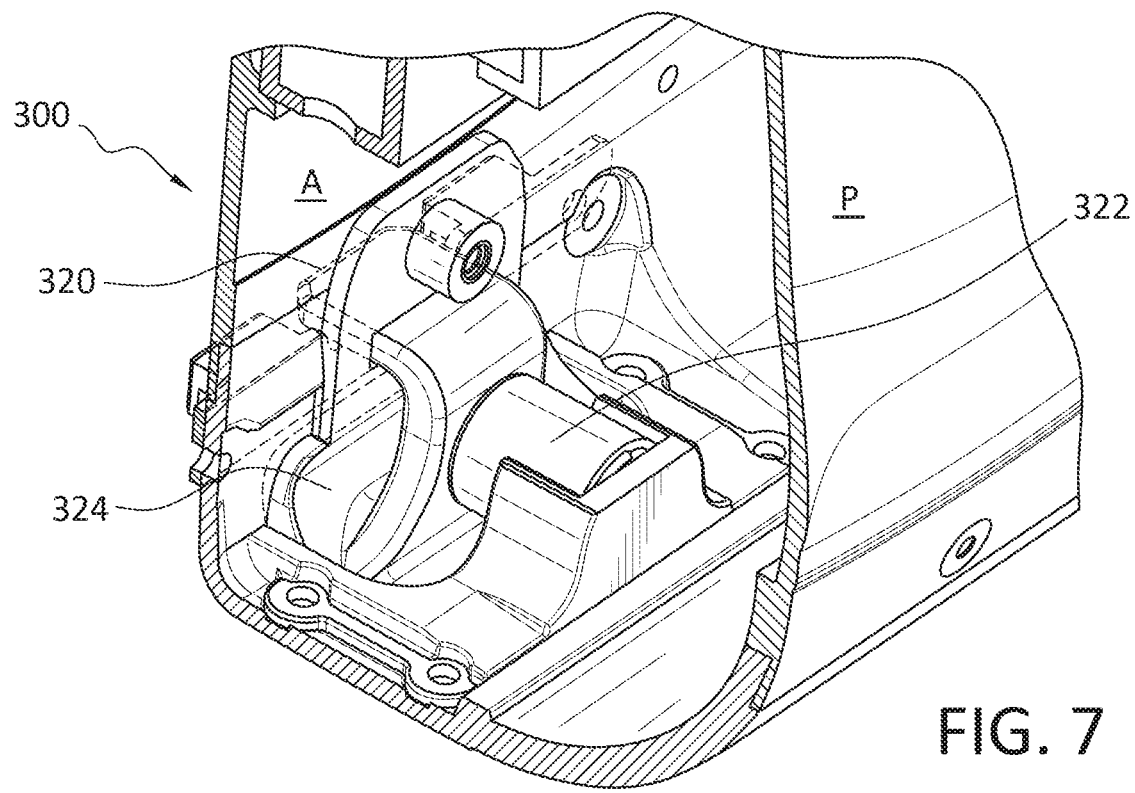
FIG. 7 is a detail view of a locking mechanism of the power supply connection system of FIG. 5.

As illustrated in FIG. 7, the locking element 320 may be configured as a protruding lip actuated by a spring 322 or other tension means, such that the force of the spring 322 secures the locking element 320 in a locking position extending from the actuation system. A locking control 324, such as a button, switch or lever, may be provided in the power supply 300, for example in a bottom portion of the power supply 300, for adapting the locking element 320 into an unlocking position, such as withdrawn into a recess of the power supply 300, against the force of the spring 324.

In an alternative embodiment, the locking element 320 may be configured as a protruding lip tilted from a locking position to an unlocking position, or otherwise moved from a locking position to an unlocking position when the locking control 324 is engaged. The locking element 320 may also be configured with a different shape or dimension, such as forming a peg, a hook, etc.

In an embodiment having a locking element 320 as described, a technician can engage the locking control 324 to adjust the locking element 320 into an unlocking position for assembling the power supply with or removing the power supply 300 from the body interface 100. Once the power supply 300 is in the desired position on the body interface 100, the technician may release or disengage the locking control 324, such that the locking element 320 is moved into the locking position.

Figure 8A:
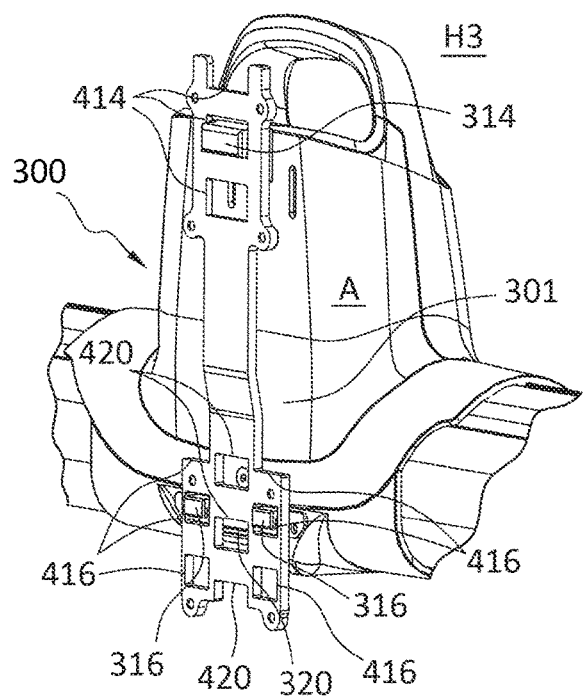
FIG. 8A is a schematic view of the power supply connection system of FIG. 5 in a first locked position on the panel connection system of FIG. 4.
Figure 8B:
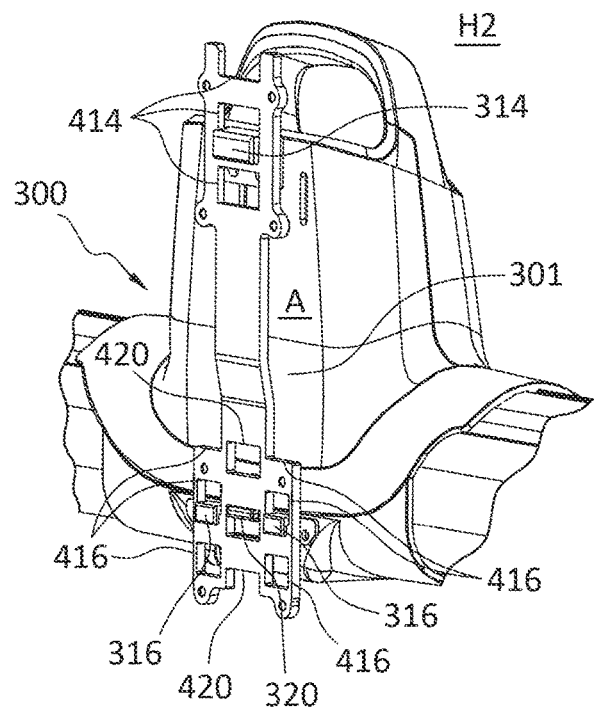
FIG. 8B is a schematic view of the power supply connection system of FIG. 5 in a first unlocked position on the panel connection system of FIG. 4.

The assembly of the power supply 300 with the body interface 100 is further illustrated in FIGS. 8A and 8B. As shown, the connection frame 410 may include the locking point 420 in addition to anchoring points 412. In an embodiment, the locking point 420 may be provided as a slot or recess between lower anchoring points 416, having an offset elevation relative to the lower anchoring points 416, such that the connection frame 410 contacts a lower surface of the anchors 316 and an upper surface of the locking element 320 in a locked configuration.

To secure the power supply 300 to the body interface 100, a technician lifts the power supply 300 while engaging the locking control 324. With the locking control 324 engaged, the locking element 320 is forced into the unlocking position, for example, in a position where the locking element does not substantially protrude from the actuation system, as shown in FIG. 8A. The power supply 300 is then lowered against the connection frame 410 of the body interface 100, so anchors 312, 314, 316 extend into and rest against anchor points 412, 414, 416.

Once the anchors 312, 314, 316 of the power supply 300 extend into and rest against anchor points 412, 414, 416 of the connection frame 410, the power supply 300 is secured by the downward force of gravity in a vertical direction. Similarly, the complementary shape of the anchors 312, 314, 316 of the power supply 300 and anchor points 412, 414, 416 of the connection frame 410 secures the power supply against forces in a horizontal plane, such as in a lateral direction. Removal is then possible only by lifting the power supply 300 in the vertical direction by application of an upward force against the downward force of gravity.

By releasing or disengaging the locking control 324, the locking element 320 is actuated by the spring 322, so the force of the spring 322 secures the locking element 320 in the locking position. In the locking position, the locking element 320 may extend into and rest against the locking point 420, as illustrated in the locked configuration of FIG. 8B. In the locked configuration of FIG. 8B, the engagement position of the locking element 320 and the locking point 420 is vertically offset relative to the engagement between anchors 312, 314, 316 and anchor points 412, 414, 416, such that the power supply 300 is secured to the connection frame 410 against an upward force in the vertical direction by the locking element 320.

Besides providing a more secure, fast and straightforward attachment between the power supply and the body interface 100, the connection system, 400 of the disclosure may be configured to improve the alignment of the power supply 300 with the body of a user. As discussed, a misalignment between the human joints and the robot joints is a common problem in the prior art, which may lead to undesired forces being exerted on the human joints resulting in discomfort or injury. To address misalignment concerns, existing exoskeletons must be manufactured and assembled precisely to the body of a user.

According to an exemplary embodiment, the exoskeleton is made configurable to the height of a user by providing a plurality of sets of anchor points 412, including a plurality of upper anchor points 414 and a plurality of lower anchor points 416, in a plurality of preset height positions H1, H2, H3. In use, a technician can optimize the vertical alignment of the power supply 300 concerning the body of the user by selecting the appropriate preset height position on the body interface 100.

By providing a plurality of anchor points 412, for example in an APO, the power supply 300 may be raised or lowered to correspond to a height of a joint of the user, to ensure alignment of the assistive system 200 with the joints of the user's body.

Figure 8C:
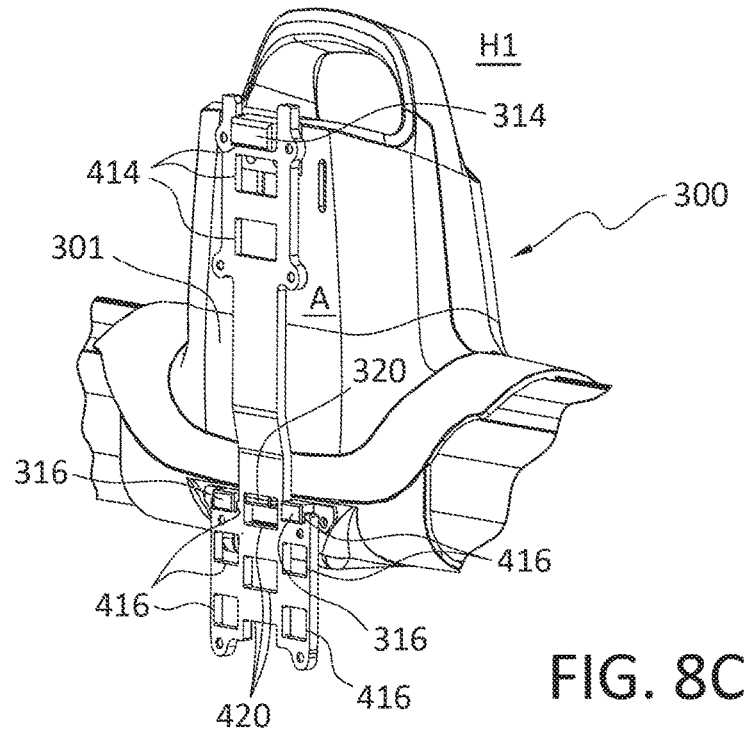
FIG. 8C is a schematic view of the power supply connection system of FIG. 5 in a second locked position on the panel connection system of FIG. 4.

The adjustment of the height of the power supply 300 on the body interface 100 is shown in FIGS. 8A-8C. The power supply 300 may be raised by a technician with the locking element 320 in the unlocking position and lowered against the connection frame 410 of the body interface 100, such that the anchors 312, 314, 316 extend into the anchor points 412, 414, 416 in FIG. 8A. Once the anchors 312, 314, 316 of the power supply 300 extend into and rest against anchor points 412, 414, 416 of the connection frame 410, the locking element 320 is adjusted to the locking position against the locking point 420, and the power supply 300 is secured in a second height position H2, as shown in FIG. 8B.

A technician may adjust the height position H1, H2, H3 of the power supply 300 in a similar manner. To remove the power supply 300 from a second height position H2 of FIG. 8B, the technician engages the locking control 324 to withdraw the locking element 320 from the locking point 420. The power supply 300 is then lifted away from the connection frame 410, removing the anchors 312, 314, 316 from the anchor points 412, 414, 416, as shown in FIG. 8A.

The power supply 300 may be raised or lowered by a technician to a desired height position H1, H2, H3, and then lowered against the connection frame 410 of the body interface 100, so the anchors 312, 314, 316 extend into the anchor points 412, 414, 416. Once the anchors 312, 314, 316 of the power supply 300 extend into and rest against anchor points 412, 414, 416 of the connection frame 410, the locking element 320 is adjusted to an extended position against locking point 420. The power supply 300 can be secured in a first height position H1, such as illustrated in FIG. 8C.

Figure 9:
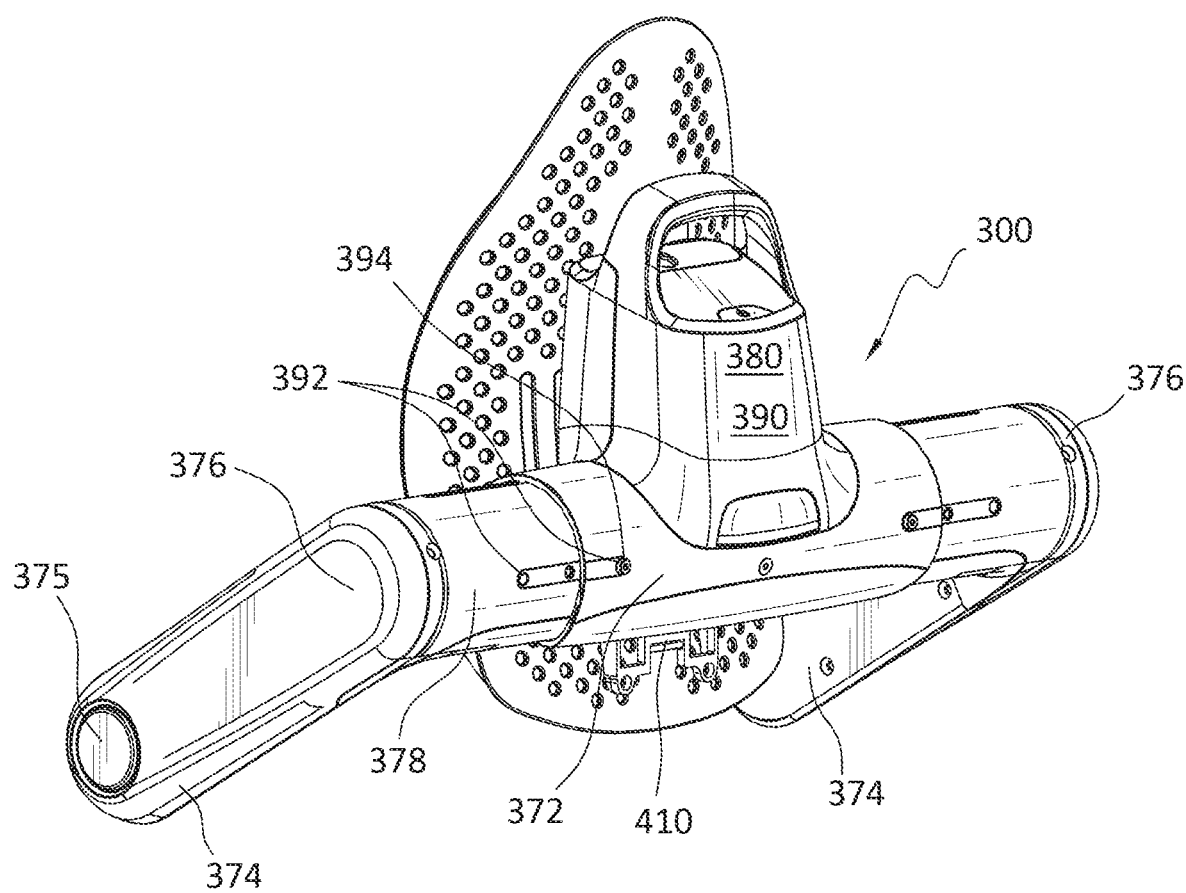
FIG. 9 is a rear perspective view of a power supply and a body interface in an attached arrangement according to an embodiment of the disclosure.

FIG. 9 illustrates the power supply 300 attached to the panel 180 of the body interface 100 according to an embodiment of the disclosure. The power supply 300 may be adjusted between the height positions of the connection frame 410 as referenced above, regarding FIGS. 8A-8C, and a corresponding adjustment occurs in the height of the transmission devices 374. In allowing a variable height position for the connection between the power supply 300 and the body interface, the transmission devices 374 may be appropriately positioned to engage the assistive system 200 dependent on the respective dimensions of the user's body rapidly.

The adjustability of the power supply 300 on the height positions H1, H2, H3 of the connection frame 410 of the body interface 100 reduces the cost and the complexity of the exoskeleton system. With a connection frame 410 having a plurality of height positions, the height of a power supply 300 relative to the body of the user may be varied in a rapid and simple manner, with no specially sized components. Rather, a single power supply 300 and body interface 100 may be manufactured for all users, with the attachment position of the power supply 300 and the body interface 100 being determined based on the individual dimensions and needs of a user.

A technician is thus enabled to use the same power supply 300, body interface 100, and assistive system 200 for a variety of users with only a quick movement of the power supply 300 being required. The improved adjustability further increases the precision of coupling and compatibility between human joints and rotation axes of the exoskeleton system. It increases the manufacturing tolerance of the components of the exoskeleton system.

According to a further embodiment, a single power supply may be manufactured and employed for all users, while the body interface the panel or other components thereof may be produced in a variety of predetermined sizes, or produced to custom fit the requirements of a given individual. As the cost of manufacturing the body interface or the panel is low relative to the actuation system, significant cost savings result from the ability to use a single power supply for all users, particularly where the power supply may be fitted to a body interface by the fast and simple connection system of the disclosure.

Figure 10:
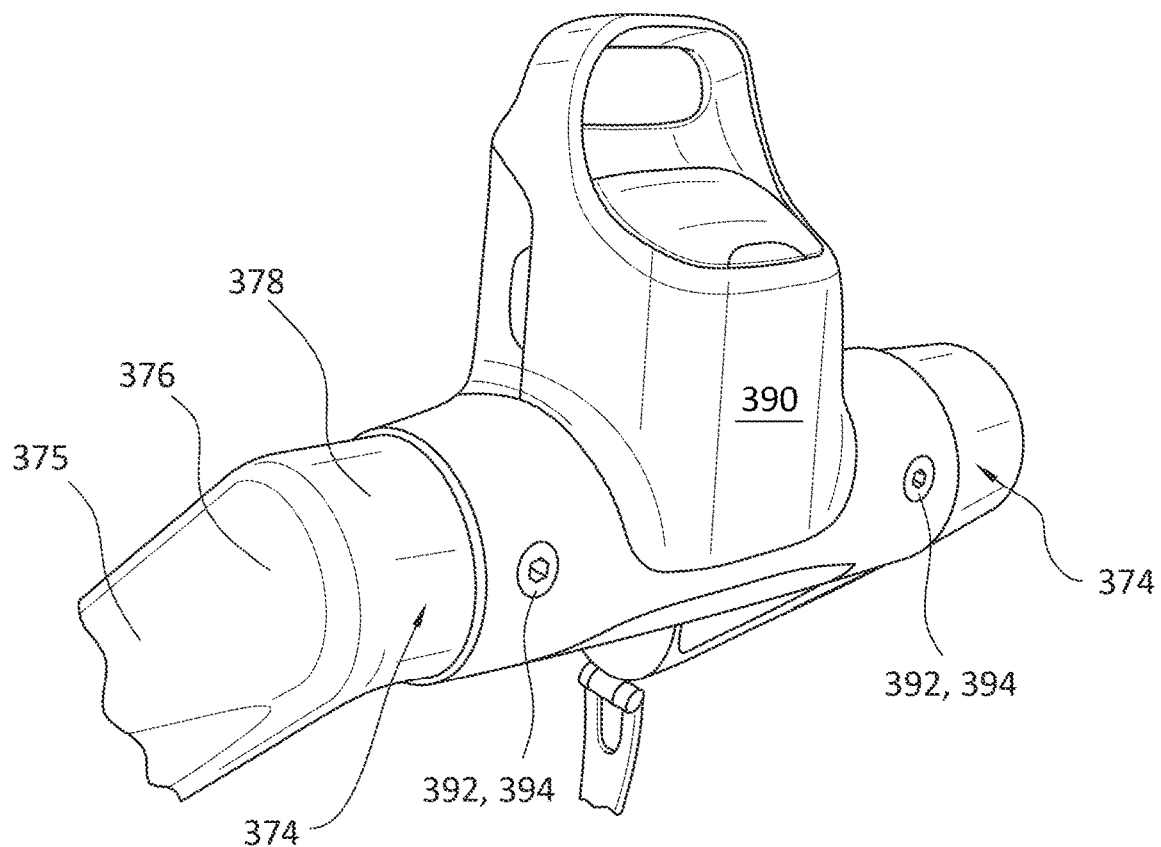
FIG. 10 is a rear perspective view of a power supply having transmission arms with adjustable width according to an embodiment of the disclosure.

The exoskeleton system of the disclosure may further be arranged for adapting to a varying width of a user, such as a width of a user's hips in an APO, by providing the power supply 300 with a width adjustment mechanism. As illustrated in FIG. 10, a width of the power supply 300 generally comprises the drive system 372 extending from the power system 380, and linked to the transmission devices 374, such as at a robotic hip joint 376 in an APO.

According to the embodiment of FIG. 10, the power supply 300 may be provided with a variable width by adapting a connection between the transmission devices 374 and the drive system 372 with at least one drive locking element 392, preferably at least two drive locking elements 392. As shown, the transmission devices 374 may comprise a transmission arm 375 and a transmission shoulder 378.

The transmission arm 375 is configured to attach to the assistive system 200, such as at a leg/hip assist mechanism 220 and/or a leg connection 240, and is linked to the drive system 372 by the transmission shoulder 378, which extends laterally from the drive system 372.

The transmission shoulder 378 is configured to have a diameter that is smaller than a diameter of a main compartment 390 of the power supply 300 from which it extends, where the main compartment 390 may include the drive system 372 and/or the power system 380. A length of the transmission shoulder 378 slidably extends within the diameter of the main compartment 390, so the connection between the transmission shoulder 378 and the drive system 372 is provided within the main compartment 390 and is adjustable in a lateral direction.

For securing the transmission shoulder 378 to the main compartment 390, the main compartment includes at least one transmission locking point 394 for cooperating with the drive locking element 392 of the transmission shoulder 378. For example, the at least one transmission locking point 394 may be configured as a recess or a slot for receiving the drive locking element 392 of the transmission shoulder 378 in a locked configuration.

The at least one drive locking element 392 may be configured as a spring-loaded protrusion on the transmission shoulder 378, so the drive locking element 392 is biased in an extended or locked configuration. The drive locking element 392 is preferably adapted to have a shape complementary to the at least one transmission locking point 394, so the, when the transmission shoulder 378 is inserted within the diameter of the main compartment 390 and the drive locking element 392, is positioned directly below the transmission locking point 394, the drive locking element 392 secures to the at least one transmission locking point 394.

Figures 11A, 11B, 11C:
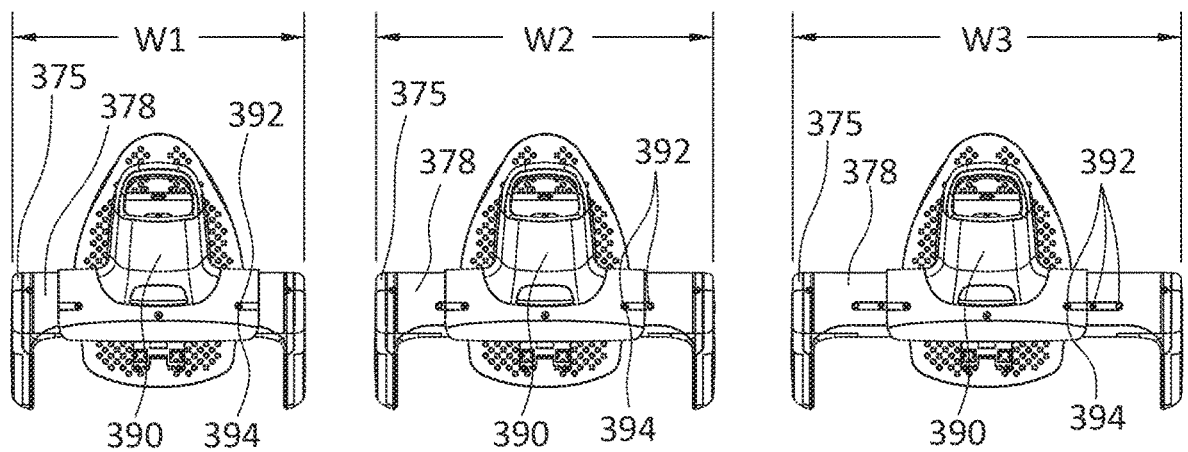
FIG. 11A is a posterior view of the power supply of FIG. 11 having transmission arms in a first width position.
FIG. 11B is a posterior view of the power supply of FIG. 11 having transmission arms in a second width position.
FIG. 11C is a posterior view of the power supply of FIG. 11 having transmission arms in a third width position.

In an embodiment according to FIGS. 11A-C, the power supply 300 may include three drive locking elements 392 on each transmission shoulder 378, the drive locking elements 392 positioned with varying distances from the transmission arm 37 corresponding to preset width positions. A single transmission locking point 394 is provided on each lateral side of the main compartment 390 of the device. At a first width position illustrated in FIG. 11A, a lateral most drive locking element 392 is engaged with the respective transmission locking point 394, for example as a spring loaded protrusion extending into a recess. Hence, the power supply has a first width W1. The additional drive locking elements are provided within the main compartment 390, so the remaining drive locking elements 392 are compressed against the spring by walls of the main compartment 390.

To adjust the width of the power supply 300, a technician may disengage the drive locking element 392, such as by depressing the protrusion against the spring, and slide the transmission shoulder 378 in or out of the main compartment 390. When the transmission shoulder 378 is moved to another preset position, a subsequent drive locking element 392 can engage the transmission locking point 394, for example at a second width W2 as illustrated in FIG. 11B or at a third width W3 as illustrated in FIG. 11C.

The embodiment depicted in FIGS. 11A-C provides a simple and intuitive mechanism for conforming the power supply 300 to the dimensions of a user. Using a slidable transmission shoulder 378 is advantageous because it provides for adjustment of the device while attached to a user, increased speed and simplicity, and reduction of material costs, while still allowing for a dynamic engagement between the body interface 100, the user, and an exoskeleton.

As discussed, FIG. 9 illustrates the power supply 300 attached to the panel 180 of the body interface 100 according to an embodiment of the disclosure. The power supply 300 may be adjusted between the height positions of the connection frame 410 as referenced above regarding FIGS. 8A-8C, and a corresponding adjustment occurs in the height of the transmission devices 374. The power supply 300 may further be adjusted between the width positions of the transmission shoulder 378 as referenced above regarding FIGS. 11A-11C, and a corresponding adjustment occurs in the width of the transmission devices 374. In allowing a variable height position for the connection between the power supply 300 and the body interface, and a variable width position for the connection between the transmission shoulder 378 and the main compartment 390, the exoskeleton system of the disclosure is easily adaptable to the dimensions of a user in at least two directions.

A technician is able to rapidly adjust the position of the power supply 300 to the user, with no devices that are custom manufactured to the dimensions of the user. In this way, the transmission devices 374 may be appropriately positioned to engage the assistive system 200 dependent on the respective dimensions of the user's body rapidly.

In a method for assembling an exoskeleton system according to the disclosure, a body interface 100 is donned in a manner similar to conventional lumbar supports or to a backpack type interface. For example, the body interface 100 may be donned by passing the arms of a user through the strap system 140, tightening the straps against shoulders of the user and tensioning the attachment system 116 about the user's torso. Once the body interface 100 is tightened to the user, a technician can lift the power supply 300 while engaging the locking control 324. With the locking control 324 engaged, the locking element 320 is forced into the unlocking position, for example in a position where the locking element does not substantially protrude from the actuation system, as shown in FIG. 8A. The power supply 300 is then lowered against the connection frame 410 of the body interface 100, so anchors 312, 314, 316 extend into and rest against anchor points 412, 414, 416. The locking element need not be constantly engaged, per the aforementioned steps. Rather depressing the le locking element may not be necessary during the donning step, but would be necessary during a doffing step.

Once the anchors 312, 314, 316 of the power supply 300 extend into and rest against anchor points 412, 414, 416 of the connection frame 410, the power supply 300 is secured by the downward force of gravity in a vertical direction. Similarly, the complementary shape of the anchors 312, 314, 316 of the power supply 300 and anchor points 412, 414, 416 of the connection frame 410 secures the power supply against forces in a horizontal plane, such as in a lateral direction. Removal is then possible only by lifting the power supply 300 in the vertical direction, by application of an upward force against the downward force of gravity.

By releasing or disengaging the locking control 324, the locking element 320 is actuated by the spring 322, so the force of the spring 322 secures the locking element 320 in the locking position. In the locking position, the locking element 320 may extend into and rest against the locking point 420, as illustrated in the locked configuration of FIG. 8B. In the locked configuration of FIG. 8B, the engagement position of the locking element 320 and the locking point 420 is vertically offset relative to the engagement between anchors 312, 314, 316 and anchor points 412, 414, 416, so the power supply 300 is secured to the connection frame 410 against an upward force in the vertical direction by the locking element 320.

The technician may then adjust the width dimension of the power supply 300, by disengaging the drive locking element 392 from the transmission locking point 394 and sliding the transmission shoulder 378 in a lateral direction until a subsequent drive locking element 392 engages the transmission locking point 394.

The adjustability of the power supply 300 on the height positions H1, H2, H3 of the connection frame 410 of the body interface 100 and on the width positions W1, W2, W3 reduces the cost and the complexity of the exoskeleton system. The adjustments may be made rapidly after the user has donned the body interface 100, and may be configured directly to the needs of the user while donning the power supply 300, with no more than one technician.

Figure 12A:
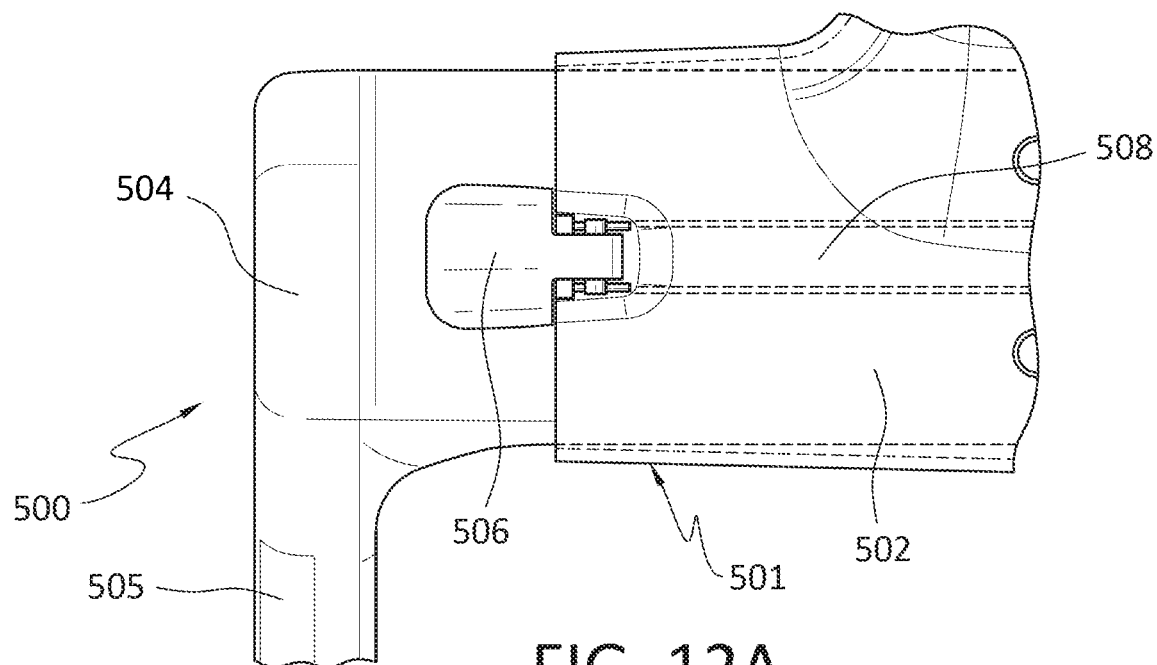
FIG. 12A is a perspective view of another width adjustment system.

FIG. 12A shows another embodiment for adjusting the width of the power supply. In this embodiment 500, the base portion 502 of the power supply housing 501 locks to the extension portion 504 with a lever 506 mounted on the base portion 502. The lever 506 may be arranged in either vertical or horizontal configurations, whereas shown the lever is in a horizontal configuration. A channel 508 is formed along the base portion 502, preferably on an inner side, along which the extension portion 504 slides to adjust width of the power supply. The extension portion 504 may carry a transmission arm 505 as in other embodiments, and both lateral sides of the power supply may include this width adjustment arrangement.

Figure 12B:
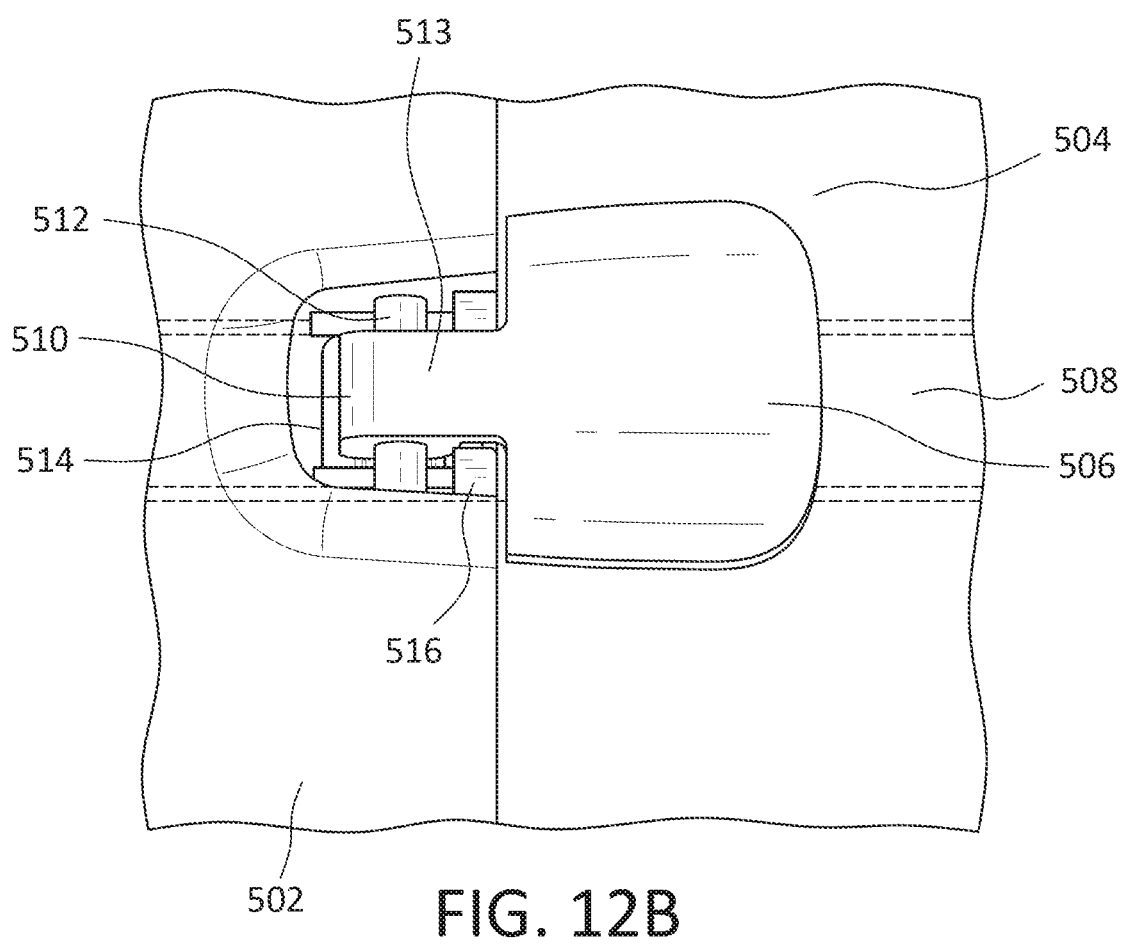
FIG. 12B is a detail view taken from FIG. 12A.

The lever 506 is shown in more detail in FIG. 12B. The lever 506 has an eccentric base 510 which enables a frictional fit of the eccentric base 510 against the extension portion 502 when the lever is pressed downwardly to prevent movement of the extension portion 504 relative to the base portion 502. When pressed downwardly, the lever arm 513 locks into a base locking element 516. The eccentric base 510 pivots about a shaft 512 and is supported by a sliding base 514. The sliding base 514 is arranged to slide within the channel 508.

Figure 13B:
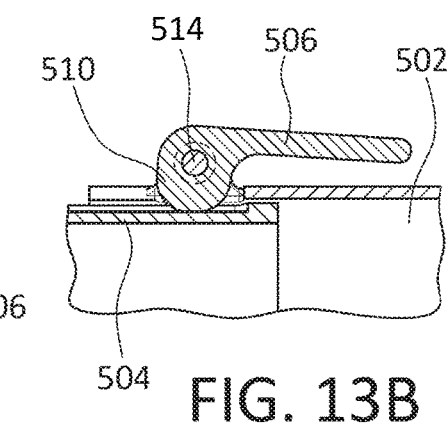
FIG. 13B is a detail view of the lever in the width adjustment system of FIG. 12A in the locked mode of FIG. 13A.
Figure 13A:
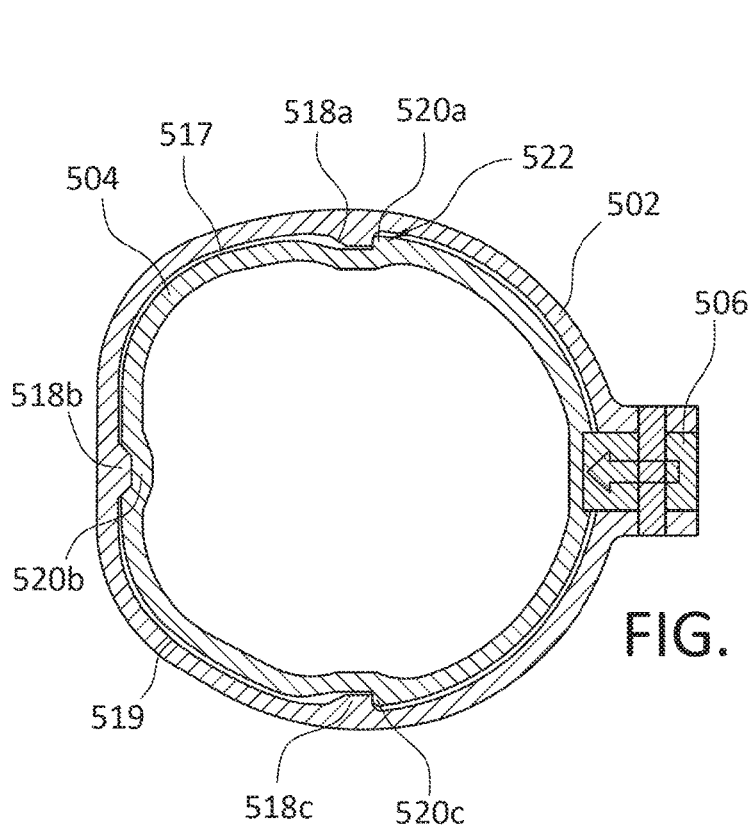
FIG. 13A is a schematic view of the width adjustment system of FIG. 12A in a locked mode.
Figure 13D:
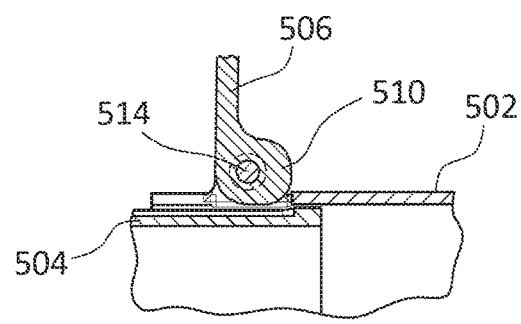
FIG. 13D is a detail view of the lever in the width adjustment system of FIG. 12B in the unlocked mode of FIG. 13C.
Figure 13C:
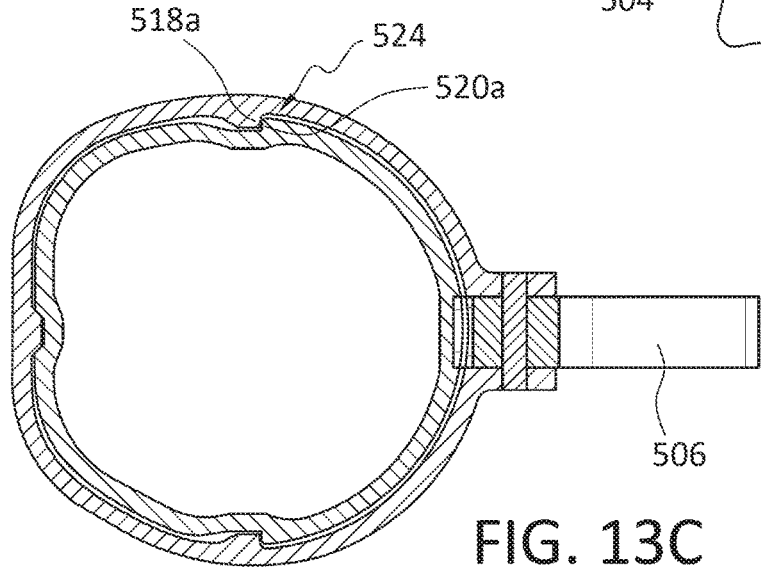
FIG. 13C is a schematic view of the width adjustment system of FIG. 12A in an unlocked mode.

FIGS. 13A-13C show how the lever presses the extension portion 504, which is located within the base portion 502. FIG. 13A shows how the lever 506, in a locked mode, urges protrusions 518a, 518b, 518c of the extension portion 504 extending circumferentially thereabout an outer surface 517 against cooperating protrusions 520a, 520b, 520c extending from an inner surface 519 of the base portion 502. The locked mode creates an interference among the cooperating protrusions 518a, 518b, 518c, 520a, 520b, 520c. FIG. 13B shows the eccentric base 510 urged against extension portion 504 to urge the cooperating protrusions 518a, 518b, 518c, 520a, 520b, 520c against one another. FIG. 13C shows the lever 506 in an unlocked mode in which the cooperating protrusions 518a, 518b, 518c, 520a, 520b, 520c are separated from one another, enabling some play 524 to adjust the adjustment portion 504 relative to the base portion 502.

FIG. 14A embodies a leg connection 550, as generally illustrated as the leg connection 240 in FIGS. 1A and 1B. In this embodiment, the cuff 552 is arranged to slidably engage a strut 554, and lock in position with a lever 556. FIG. 14B shows the leg connection 550 in an unlocked mode whereby turning of the lever 556 relieves the frictional fit of the eccentric base 558 against the strut 554. A base 560 connects the cuff 552 to the strut 554, and carries the lever 556. FIG. 14C shows the leg connection 550 in a locked mode.

A technician is thus enabled to use the same power supply 300, body interface 100 and assistive system 200 for a variety of users with only a quick movement of the power supply 300 being required. The improved adjustability further increases the precision of coupling and compatibility between human joints and rotation axes of the exoskeleton system, and increases the manufacturing tolerance of the components of the exoskeleton system.

According to a further embodiment, a single power supply may be manufactured and employed for all users, while the body interface the panel or other components thereof may be produced in a variety of predetermined sizes, or produced to custom fit the requirements of an individual. As the cost of manufacturing the body interface or the panel is low relative to the actuation system, significant cost savings result from the ability to use a single power supply for all users, particularly where the power supply may be fitted to a body interface by the fast and simple connection system of the disclosure.

It is to be understood that not necessarily all objects or advantages may be achieved under any embodiment of the disclosure. Those skilled in the art will recognize that the body interface may be embodied or carried out, so it achieves or optimizes one advantage or group of advantages as taught without achieving other objects or advantages as taught or suggested herein.

The skilled artisan will recognize the interchangeability of various disclosed features. Besides the variations described, other known equivalents for each feature can be mixed and matched by one of ordinary skill in this art to construct a body interface under principles of the present disclosure. It will be understood by the skilled artisan that the features described may be adapted to orthopedic devices. Hence, this disclosure and the embodiments and variations thereof are not limited to a body interface but can be utilized in any orthopedic device.

Although this disclosure describes certain exemplary embodiments and examples of a body interface, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above, and may be extended to body interfaces and orthopedic devices, and other applications that may employ the features described.

The invention claimed is:

1. An exoskeleton system, comprising:
    a body interface configured for securing to a back of a user and including a panel provided with at least one anchoring slot and at least one locking slot, the panel defining a center axis;
    a power supply adapted to provide motion control to the exoskeleton system;
    at least one anchor and corresponding in location to the at least one anchoring slot, the at least one anchor configured to fit through at least one anchoring slot to engage the body interface;
    at least one locking element extending from the power supply and corresponding to the at least one locking slot of the panel, the at least one locking element having a locking control arranged to be selected to a locking position for engagement with the body interface and selected to an unlocking position for disengagement from the body interface.

2. The exoskeleton system of claim 1, wherein the power supply includes a housing from which the at least one anchor and the at least one locking element extend.

3. The exoskeleton system of claim 2, wherein the at least one anchor comprises at least two anchors located at different locations relative to the center axis of the panel.

4. The exoskeleton system of claim 1, wherein the at least one anchoring slot is located above the at least one locking slot relative to the center axis of the panel.

5. The exoskeleton system of claim 1, wherein the at least one anchor forms a protruding lip defining a right angle at a terminal end.

6. The exoskeleton system of claim 5, wherein a length of the at least one anchor is the same as a thickness of the at least one anchoring slot such the at least one anchor is adapted to fit and extend through the at least one anchoring slot.

7. The exoskeleton system of claim 1, wherein the power supply further comprises a housing including a locking recess, and an actuation system including a drive system linked to at least one transmission arm,
    wherein the at least one transmission arm is slidably arranged within the housing and includes a drive locking part protruding therefrom, the drive locking part corresponding to the locking recess and adjustable to a drive locking position and a drive unlocking position by actuation of the drive locking part.

8. The exoskeleton system of claim 1, wherein the panel includes a connection frame oriented along the center axis thereof, the connection frame forming the at least one anchoring slot and at least one locking slot.

9. The exoskeleton system of claim 8, wherein the at least one anchoring slot includes at least two anchoring slots spaced apart from one another at different heights along the center axis of the panel to provide for securing the panel along a center axis of the power supply.

10. The exoskeleton system of claim 8, wherein the at least one locking slot includes two locking slots spaced apart from one another at different heights along the center axis of the panel to provide for securing the panel along a center axis of the power supply.

11. The exoskeleton system of claim 8, wherein the at least one locking slot defines at least two sets of locking slots spaced apart from one another at different heights along the center axis of the panel, each set of locking slots includes at least two locking slots.

12. The exoskeleton system of claim 11, wherein each set of locking slots includes first and second locking slots located on opposed sides of the center axis and at a same height along the center axis of the panel.

13. The exoskeleton system of claim 12, wherein each set of locking slots includes a third locking slot located centrally along the center axis of the panel and the first and second locking slots are located on opposed sides of the third locking slot.

14. The exoskeleton system of claim 13, wherein the third locking slot is located at a different height along the center axis of the panel relative to the first and second slots.

15. The exoskeleton system of claim 8, wherein the connection frame is formed from and integrated with the panel.

16. An exoskeleton system for connecting to a power supply adapted to provide motion control to said exoskeleton system, the exoskeleton system comprising:
    a body interface configured for securing to a back of a user and including a panel provided with at least one anchoring slot and at least one locking slot, the panel defining a center axis;

at least one anchor and corresponding in location to the at least one anchoring slot, the at least one anchor configured to fit through at least one anchoring slot to engage the body interface;

at least one locking element arranged to extend from the power supply and correspond to the at least one locking slot of the panel, the at least one locking element having a locking control arranged to be selected to a locking position for engagement with the body interface and selected to an unlocking position for disengagement from the body interface.

17. The exoskeleton system of claim 16, wherein the at least one anchoring slot includes at least two anchoring slots spaced apart from one another at different heights along the center axis of the panel to provide for securing the panel to the power supply.

18. The exoskeleton system of claim 16, wherein the at least one locking slot includes two locking slots spaced apart from one another at different heights along the center axis of the panel to provide for securing the panel to the power supply.

19. The exoskeleton system of claim 16, wherein the at least one locking slot defines at least two sets of locking slots spaced apart from one another at different heights along the center axis of the panel, each set of locking slots includes at least two locking slots;

wherein each set of locking slots includes first and second locking slots located on opposed sides of the center axis of the panel and at a same height along said center axis.

20. An exoskeleton system for connecting to a power supply adapted to provide motion control to said exoskeleton system, the exoskeleton system comprising:

a body interface configured for securing to a back of a user and including a panel provided with at least one anchoring slot and at least one locking slot, the panel defining a center axis;

at least one anchor and corresponding in location to the at least one anchoring slot, the at least one anchor configured to fit through at least one anchoring slot to engage the body interface;

at least one locking element arranged to extend from the power supply and correspond to the at least one locking slot of the panel, the at least one locking element having a locking control arranged to be selected to a locking position for engagement with the body interface and selected to an unlocking position for disengagement from the body interface;

wherein the at least one anchoring slot is located above the at least one locking slot relative to the center axis defined by the panel;

wherein the at least one anchor forms a protruding lip defining a right angle at a terminal end.

* * * * *

UNITED STATES PATENT AND TRADEMARK OFFICE
CERTIFICATE OF CORRECTION

Page 1 of 1

PATENT NO. : 12,156,845 B2
APPLICATION NO. : 17/604632
DATED : December 3, 2024
INVENTOR(S) : Kristin Asa Thorisdottir and David Sandahl It is certified that error appears in the above-identified patent and that said Letters Patent is hereby corrected as shown below:

On the Title Page

Item (65):
Add Related U.S. Application Data:
"Provisional Application No. 62/837,356, filed on April 23, 2019."

Signed and Sealed this
Thirteenth Day of May, 2025

Coke Morgan Stewart
*Acting Director of the United States Patent and Trademark Office*